United States Patent [19]

Scholl

[11] Patent Number: 4,665,178

[45] Date of Patent: May 12, 1987

[54] 2,5-DI-(4'-ISOCYANATOBUTYL)-3,6-DIMETHYLPYRAZINE AND A PROCESS FOR ITS PRODUCTION

[75] Inventor: Hans-Joachim Scholl, Colonge, Fed. Rep. of Germany

[73] Assignee: Bayer Aktiengesellschaft, Leverkusen, Fed. Rep. of Germany

[21] Appl. No.: 762,644

[22] Filed: Aug. 5, 1985

[30] Foreign Application Priority Data

Aug. 16, 1984 [DE] Fed. Rep. of Germany ....... 3429962

[51] Int. Cl.$^4$ ........................................... C07D 241/12
[52] U.S. Cl. .................................... 544/336; 528/67; 564/160
[58] Field of Search ......................................... 544/336

[56] References Cited

U.S. PATENT DOCUMENTS 4,107,199  8/1978  Konig ..................................... 528/44
4,122,128 10/1978  Lehman .............................. 525/112
4,150,229  4/1979  Rajappa et al. ...................... 544/336

FOREIGN PATENT DOCUMENTS 0113044  7/1984  European Pat. Off. .

Primary Examiner—Mark L. Berch
Assistant Examiner—William A. Teoli, Jr.
Attorney, Agent, or Firm—Gene Harsh; Joseph C. Gil; Lyndanne M. Whalen

[57] ABSTRACT

2,5-di-(4'-isocyanatobutyl)-3,6-dimethylpyrazine which corresponds to the formula

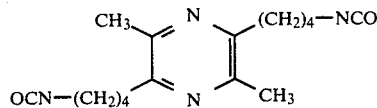

is produced by phosgenating 2,5-di-(4'-aminobutyl)-3,6-dimethylpyrazine. The 2,5-di-(4'-isocyanatobutyl)-3,6-dimethylpyrazine is particularly useful as an isocyanate component for the production of polyurethanes.

1 Claim, No Drawings

2,5-DI-(4'-ISOCYANATOBUTYL)-3,6-DIMETHYL-PYRAZINE AND A PROCESS FOR ITS PRODUCTION

FIELD OF THE INVENTION

The present invention relates to 2,5-di-(4'-isocyanatobutyl)-3,6-dimethylpyrazine (DIDP) and to a process for the production thereof.

SUMMARY OF THE INVENTION

It is an object of the present invention to provide the new composition 2,5-di-(4'-isocyanatobutyl)-3,6-dimethylpyrazine.

It is also an object of the present invention to provide a process for the production of 2,5-di-(4'-isocyanatobutyl)-3,6-dimethylpyrazine.

It is another object of the present invention to provide an isocyanate component for the production of isocyanate polyaddition products which isocyanate component incorporates into the skeleton of the product pyrazine structural units as hard segments.

It is a further object of the present invention to provide an isocyanate component for the production of polyurethanes which component imparts valuable mechanical properties to the polyurethane.

It is yet another object of the present invention to provide an isocyanate component for the production of polyurethanes which component may be converted by quaternization or by neutralization into ternary or quaternary ammonium groups and thereby render the polyurethane into which the component is incorporated dispersible in water.

These and other objects which will be apparent to those skilled in the art are accomplished by phosgenating 2,5-di-(4'-aminobutyl)-3,6-dimethylpyrazine to produce 2,5-di-(4'-isocyanatobutyl)-3,6-dimethylpyrazine corresponding to the formula

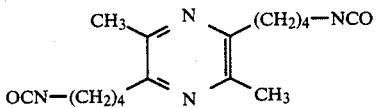

The 2,5-di-(4'-isocyanatobutyl)-3,6-dimethylpyrazine thus produced may then be reacted with a compound containing isocyanate-reactive hydrogen atoms to form isocyanate polyaddition products such as polyurethanes.

DETAILED DESCRIPTION OF THE INVENTION

This invention relates to 2,5-di-(4'-isocyanatobutyl)-3,6-dimethylpyrazine (DIDP) corresponding to the formula

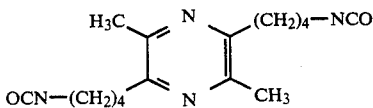

The invention also relates to a process for the production of 2,5-di-(4'-isocyanatobutyl)-3,6-dimethylpyrazine in which 2,5-di-(4'-aminobutyl)-3,6-dimethylpyrazine (DADP) or an addition compound thereof is phosgenated.

DIDP is a new diisocyanate containing aliphatically bound isocyanate groups and incorporated tertiary nitrogen atoms. DIDP is thus a valuable starting material for the production of polyurethane plastics by the isocyanate polyaddition process. When DIDP is used as an isocyanate component in the production of polyurethane plastics, pyrazine structural units which act as hard segments are incorporated in the polyurethane skeleton. Valuable mechanical properties are thereby imparted to the polyurethane. Such pyrazine structural units can be converted by quaternization or by neutralization into ternary or quaternary ammonium groups so that the polyurethanes containing incorporated DIDP may readily be converted into polyadducts dispersible in water.

The starting material for the process of the present invention is DADP which corresponds to the formula

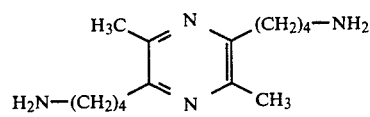

DADP may be converted into DIDP in known manner by phosgenation. To this end, it is possible to use the known "base process", the known "hydrogen chloride process" and also the known "carbon dioxide process". In every case, chlorobenzene and/or o-dichlorobenzene is (are) the preferred reaction medium. The phosgenation temperature is generally in the range from $-10°$ C. to $+180°$ C. and preferably in the range from $0°$ C. to $150°$ C. In the "base process" for phosgenation, the free diamine is directly reacted with phosgene. In this case, it is advisable to apply the principle of "cold-hot phosgenation", i.e., the corresponding carbamic acid chloride is initially produced by reacting the DADP with phosgene at a comparatively low temperature (within the ranges specified above) and is subsequently converted into DIDP by the continued addition of phosgene at an elevated temperature (within the ranges specified above). Where the "hydrogen chloride process" or the "carbon dioxide process" is used to phosgenate DADP, the corresponding adduct is preferably first produced from DADP and HCl or $CO_2$ at a low temperature (within the range of $-10°$ to $180°$ C.), and subsequently converted into DIDP by the continued addition of phosgene at an elevated temperature (within the ranges of $-10$ to $180°$ C.). The DIDP is preferably prepared in pure form by working up the phosgenated reaction mixture by distillation after any solid secondary products present have been removed by filtration. DIDP accumulates in the form of a liquid which can be distilled at $180°-185°$ C./1 mbar. DIDP shows only a minimal tendency towards crystallization at room temperature.

The DADP used as the starting material in the process of the present invention may be produced, for example, by acid hydrolysis of 3,7-bisacetamino-2-heptanone, followed by cyclocondensation and the removal of hydrogen from the 3,7-diamino-2-heptanone accumulating (in salt form) as the hydrolysis product under the effect of strong bases.

The acid hydrolysis of 3,7-bisacetamino-2-heptanone may be carried out, for example, by treating solutions of 3,7-bisacetamino-2-heptanone in water with strong acids at reflux temperature (i.e., at around $100°$ C.). Suitable strong acids include organic and inorganic acids such as toluene sulfonic acid, sulfuric acid, or, preferably, hydrochloric acid. The acid is generally used in a quantity of from 2 to 12 moles (preferably from 3 to 6 moles) for each mole of 3,7-bisacetamino-2-heptanone. The acidic hydrolysis reaction is generally over after 2 to 6 hours. It is preferred to use a volatile acid such as hydrochloric acid in the acid hydrolysis reaction because the excess acid or most of the excess acid may be removed from the reaction mixture by distillation before the subsequent condensation reaction (carried out in a basic medium). Neutralization of the acid is therefore unnecessary.

After the preparation of the acid hydrolysis mixture and preferably after the removal by distillation of readily volatile constituents (including most of the water and the preferably volatile acid), a strong base is added until the mixture shows a strongly basic reaction. Suitable strong bases include organic and inorganic bases such as triethylamine, sodium hydroxide, potassium hydroxide and the corresponding alkali carbonates. Strong inorganic bases such as sodium hydroxide and potassium hydroxide are preferred. A 0.5 to 10 molar excess (preferably, a 1- to 6-molar excess) of the base for each mole of 3,7-bis-acetamino-2-heptanone is generally used. "Excess" as used herein is the quantity of base which exceeds that quantity required to neutralize the free acid and the acid bound to the diamine present in the reaction mixture. After addition of the base, the basic reaction mixture is generally kept at a temperature in the range from 0° to 60° C., preferably at room temperature. The cyclocondensation reaction which takes place spontaneously is accompanied by the elimination of hydrogen and leads directly to formation of DADP. The reaction mixture obtained on completion of the reaction may be worked up, for example, by extracting the reaction product from the strongly basic, salt-containing aqueous solution using water-insoluble solvents (such as diethyl ether, benzene, toluene or chlorobenzene) and subsequently removing the extractant.

The above-described process for the production of DADP may be illustrated by the following reaction scheme:

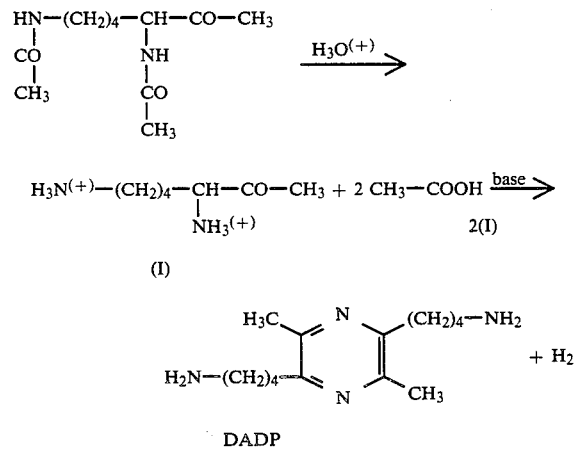

DADP

The 3,7-bisacetamino-2-heptanone used in the production of the DADP may be obtained, for example, by reacting L-lysine in free form and/or in the form of its hydrogen chloride salt with acetic acid anhydride in the presence of a tertiary organic amine base and in the presence of a 4-aminopyridine derivative. The acetic acid anhydride may be used in a quantity of from 4 to 10 moles for each mole of L-lysine and/or L-lysine hydrochloride. However, it is preferably used in a quantity of from 6 to 8 moles. Suitable tertiary organic amine bases include trialkylamines containing $C_2$-$C_6$-alkyl groups. Triethylamine is preferred. From 3 to 8 moles (preferably from 4 to 6 moles) of a tertiary organic amine base may be used for each mole of L-lysine and/or L-lysine hydrochloride. Suitable 4-aminopryidine derivatives include those corresponding to the formula

in which $R_1$ and $R_2$ independently of one another represent a single-bonded $C_1$-$C_6$-alkyl radical or, together, represent a double-bonded $C_3$-$C_5$-alkyl radical. N,N-dimethyl-4-aminopyridine or 4-pyrrolidinopyridine is preferably used. From 0.1 to 5 wt % (preferably from 0.5 to 3 wt %), based on L-lysine and/or L-lysine hydrochloride, of a 4-aminopyridine derivative may be used. The reaction is generally carried out at a temperature in the range from 20° to 100° C., preferably from 30° to 70° C.

The reaction mixture containing 3,7-bisacetamino-2-heptanone obtained on completion of the above-described reaction may be worked up, for example, by filtering off any precipitated hydrochloride of the tertiary organic amine base and removing low-boiling fractions in vacuo from the filtrate or, if no solid constituents are present, from the reaction mixture as a whole. The remaining crude product may then be stirred into a suitable solvent, such as ethyl acetate or toluene, and then filtering off, washing and drying the deposit formed. The production of 3,7-bisacetamino-2-heptanone by this method is described in detail in Example 1 below.

The fact that DIDP can be selectively produced in high yields by the process of the present invention is surprising because the DADP used as starting material contains heterocyclically bound basic ring nitrogen atoms. Such heterocyclically bound basic ring nitrogen atoms would be expected to catalyze undesirable secondary reactions involving the isocyanate groups formed at the high temperatures used for phosgenation and working up.

DIDP is a valuable synthesis component for the production of polyurethane plastics. The new diisocyanate may be used instead of or together with known diisocyanates in all known processes for the production of polyurethane plastics. The new diisocyanate contains incorporated basic nitrogen atoms. It is therefore particularly suitable for the production of self-dispersible, cationically modified polyurethanes from the starting materials normally employed for that purpose because the incorporated basic nitrogen atoms can be converted into hydrophilic amino groups by a simple quaternization reaction or neutralization reaction. Cationically modified polyurethanes such as these may be produced, for example, by the process disclosed in U.S. Pat. No. 3,479,310.

The invention is further illustrated, but is not intended to be limited by the following examples in which all parts and percentages are by weight unless otherwise specified.

EXAMPLES

EXAMPLE 1

(Production of 3,7-bisacetamino-2-heptanone)

365 g of L-lysine hydrochloride and 5 g of 4-pyrrolidinopyridine were introduced while stirring into a mixture of 1230 g of acetic acid anhydride and 810 g of triethylamine. The reaction temperature was kept at 40° to 50° C. until the evolution of gas was over. The triethylamine hydrochloride which precipitated was then filtered off and the filtrate freed in vacuo from low-boiling fractions.

The crude product remaining was stirred into 3 liters of ethyl acetate, the deposit formed was filtered under suction, washed with ethyl acetate and dried. 3,7-bisacetamino-2-heptanone melting at 111 to 113° C. was obtained in a yield of 402 g (88% of the theoretical).

| Analysis:    | % C  | % H | % N  |
|--------------|------|-----|------|
| Found:       | 57.7 | 8.7 | 12.2 |
| Calculated:  | 57.9 | 8.8 | 12.3 |

EXAMPLE 2

(Production of DADP)

114 g of 3,7-bisacetamino-2-heptanone were hydrolyzed under reflux conditions for 5 h in 0.4 l of 18% hydrochloric acid. Volatile constituents were then separated off in vacuo until about 200 ml of crude solution remained. 500 g of 45% sodium hydroxide were then introduced into the crude solution remaining with vigorous stirring and cooling with ice at a rate such that the temperature did not exceed 20° C. After stirring for 30 minutes, the aqueous phase was extracted in portions by shaking with chlorobenzene until all of the crude amine formed had been extracted (approx. 0.5 l of chlorobenzene) and then dried over calcium carbonate. Separation of the chlorobenzene left 58 g of crude amine (purity 94%, as determined by gas chromatography) which is suitable for phosgenation either as such or even after purification by distillation.

58 g of crude amine were subjected to thin-layer distillation (heating bath 210° C., 1 mbar, passover at 170° to 175° C.), giving 54.3 g of 2,5-di-(4'-aminobutyl)-3,6-dimethylpyrazine (DADP) in the form of a yellowish liquid (total yield 87%).

| Analysis:   | % C  | % H  | % N  |
|-------------|------|------|------|
| Found:      | 67.0 | 10.4 | 22.1 |
| Calculated: | 67.2 | 10.4 | 22.4 |

(Based on $C_{14}H_{26}N_4$).

EXAMPLE 3

(Production of DADP)

114 g of 3,7-bisacetamino-2-heptanone were hydrolyzed for 6 h under reflux conditions in 0.5 l of 18% hydrochloric acid. Volatile constituents were then separated off in vacuo, leaving 110 g of residue which was washed with 100 ml of acetone. 100 ml of water were then added to the residue, followed by the dropwise introduction with vigorous stirring and cooling (with ice at 0° to 10° C.) of 400 g of 45% sodium hydroxide. After stirring for 1 hour at room temperature, the amine formed was extracted in portions with toluene, followed by drying over potassium carbonate. Separation of the toluene left 61 g of crude amine which had a purity of 96% as determined by gas chromatography.

EXAMPLE 4

(Process according to the invention)

A solution of 50 g of the diamine produced in accordance with Example 2 in 1950 g of chlorobenzene was introduced into the reaction vessel. 20 g of HCl gas were then passed over the surface of the liquid with stirring at 0° C. 50 g of phosgene were then incorporated by condensation at 0° C. The reaction mixture was then heated to 50° C. over a period of 60 minutes, during which a gentle stream of phosgene was introduced (approx. 10 g/h). The mixture was then heated to 70° C. in the next 60 minutes and subsequently brought to reflux temperature over a period of 100 minutes during which phosgene was introduced at a rate of approx 20 g/h. The mixture was stirred for 16 h under these conditions. Unreacted phosgene was blown out with nitrogen while the mixture cooled to room temperature. After filtration of the mixture, the filtrate was freed from the solvent in vacuo and the crude product subjected to thin-layer distillation (heating bath 210° C., 1 mbar, passover at 180°–185° C.) 2,5-di-(4'-isocyanatobutyl)-3,6-dimethylpyrazine (DIDP) with an NCO content of 27.9% (theoretical 27.8%) was obtained in a yield of 40 g (66%).

EXAMPLE 5

(Process according to the invention)

A solution of 50 g of the diamine produced in accordance with Example 3 in 950 g of o-dichlorobenzene was introduced into the reaction vessel. 15 g of HCl gas were then passed over the surface of the liquid with stirring at 0° C. 50 g of phosgene were then incorporated by condensation at 0° C. The mixture was then heated to 50° C. over a period of 50 minutes during which a gentle stream of phosgene (approx. 10 g/h) was introduced. The mixture was heated to 70° C. in the next 50 minutes and subsequently brought to 135° C. over a period of 60 minutes during which phosgene was introduced at a rate of 20 g/h. The mixture was stirred for 8 h at 135°–140° C. Unreacted phosgene was blown out with nitrogen while the mixture cooled to room temperature. After filtration of the mixture, the filtrate was freed from the solvent in vacuo and the crude product subjected to thin-layer distillation (heating bath 210° C., 1 mbar, passover at 180°–185° C.). 33 g of 2,5-di-(4'-isocyanatobutyl)-3,6-dimethylpyrazine (DIDP) containing 27.5% of NCO (theoretical 27.8) were obtained in the form of a yellowish liquid which gradually crystallized at room temperature.

The structure of the product was additionally confirmed by conversion with ethanol into the bisethyl urethane. M.p. 99°–100° C.

| Analysis:   | % C  | % H | % N  |
|-------------|------|-----|------|
| Found:      | 60.8 | 8.7 | 14.1 |
| Calculated: | 60.9 | 8.6 | 14.2 |

(Based on $C_{20}H_{34}N_4O_4$).

EXAMPLE 6

(Use)

(6a) Production of an NCO prepolymer solution

An NCO-terminated polyester prepolymer having an NCO content of 4.4% was prepared from 123 g of a polyester diol [(molecular weight 1700) based on adipic acid, 1,6-hexane diol and neopentyl glycol (ratio by weight of hexane diol to neopentyl glycol 65:35)], 4.2 g of a monohydric polyether alcohol [(molecular weight 2150) obtained by alkoxylating n-butanol using a mixture of ethylene oxide and propylene oxide in a ratio by weight of 80:20] and a mixture of 15 g of DIDP [prepared in accordance with Example 4] and 17.9 g of 1,6-diisocyanatohexane by stirring the starting components for about 90 minutes at 100° C. The prepolymer melt was then dissolved in acetone to form a 46% solution.

(6b) Preparation of an aqueous anionic polyester urethane urea dispersion 5.61 g of isophorone diamine in 20 ml of acetone, 0.55 g of hydrazine hydrate and 5.39 g of 2-aminoethyl-β-aminoethane sulfonic acid sodium salt (in the form of a 20% solution in water) were added at 2 minute intervals with stirring at around 45° C. to the entire acetone solution of the NCO-terminated prepolymer prepared in 6a). After another 7 minutes, the constituents were dispersed over a period of about 3 minutes in 314 g of deionized water. The acetone was distilled off in vacuo. The dispersion was diluted with 160 ml of water.

The anionic-nonionic polyester urethane urea dispersion obtained had the following data:

Solids content: 30.3%.
pH-value: 6.8.
Particle size: 390 nm.
$SO_3^-$ content: 0.7%.
Viscosity (25° C.): 6500 mPas (Haake VT-02 viscosimeter, spindle #3).

On drying, the dispersion produced a clear, glossy, soft and highly elastic coating. The material is suitable for coating textiles, leather and other substrates.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

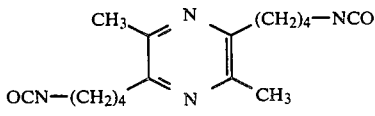

What is claimed is:

1. 2,5-di-(4'-isocyanatobutyl)-3,6-dimethylpyrazine corresponding to the formula